United States Patent
Hill

(10) Patent No.: US 10,018,560 B2
(45) Date of Patent: Jul. 10, 2018

(54) SYSTEM AND METHOD FOR HYPERSPECTRAL IMAGING METROLOGY

(71) Applicant: KLA-Tencor Corporation, Milpitas, CA (US)

(72) Inventor: Andrew V. Hill, Berkley, CA (US)

(73) Assignee: KLA-Tencor Corporation, Milpitas, CA (US)

(*) Notice: Subject to any disclaimer, the term of this patent is extended or adjusted under 35 U.S.C. 154(b) by 13 days.

(21) Appl. No.: 15/233,648

(22) Filed: Aug. 10, 2016

(65) Prior Publication Data

US 2017/0219487 A1    Aug. 3, 2017

Related U.S. Application Data

(60) Provisional application No. 62/365,120, filed on Jul. 21, 2016, provisional application No. 62/290,157, filed on Feb. 2, 2016.

(51) Int. Cl.
| | |
|---|---|
| *G02B 27/10* | (2006.01) |
| *G01N 21/47* | (2006.01) |
| *G02B 3/00* | (2006.01) |
| *G02B 27/42* | (2006.01) |
| *G01N 21/84* | (2006.01) |

(52) U.S. Cl.
CPC ..... *G01N 21/4795* (2013.01); *G01N 21/4788* (2013.01); *G02B 3/0006* (2013.01); *G02B 27/10* (2013.01); *G02B 27/1013* (2013.01); *G02B 27/4205* (2013.01); *G01N 2021/4709* (2013.01); *G01N 2021/4711* (2013.01); *G01N 2021/8461* (2013.01)

(58) Field of Classification Search
CPC .......... G02B 27/1013; G02B 27/10; G02B 27/4205; G02B 3/0006; G01N 21/4795; G01N 21/4788; G01N 2021/4709; G01N 2021/4711; G01N 2021/8461
USPC .......................................................... 359/15
See application file for complete search history.

(56) References Cited

U.S. PATENT DOCUMENTS

| | | | | |
|---|---|---|---|---|
| 6,477,293 | B1* | 11/2002 | Golub | G02B 6/2931 385/15 |
| 9,041,930 | B1 | 5/2015 | Young et al. | |
| 9,366,573 | B2* | 6/2016 | Geelen | G01J 3/513 |
| 9,696,137 | B2* | 7/2017 | Braker | G01B 11/2518 |
| 9,848,135 | B2* | 12/2017 | Geelen | H04N 5/332 |
| 2007/0096008 | A1 | 5/2007 | Akins et al. | |

(Continued)

*Primary Examiner* — William R Alexander

(74) *Attorney, Agent, or Firm* — Suiter Swantz pc llo

(57) ABSTRACT

A metrology system includes an illumination source configured to generate an illumination beam, one or more illumination optics configured to direct the illumination beam to a sample, one or more collection optics configured to collect illumination emanating from the sample, a detector, and a hyperspectral imaging sub-system. The hyperspectral imaging sub-system includes a dispersive element positioned at a pupil plane of the set of collection optics configured to spectrally disperse the collected illumination, a lens array including an array of focusing elements, and one or more imaging optics. The one or more imaging optics combine the spectrally-dispersed collected illumination to form an image of the pupil plane on the lens array. The focusing elements of the lens array distribute the collected illumination on the detector in an arrayed pattern.

33 Claims, 6 Drawing Sheets

(56) References Cited

U.S. PATENT DOCUMENTS

2008/0239065 A1* 10/2008 Momonoi .......... G02B 27/2214
                                                      348/49
2010/0328659 A1   12/2010 Bodkin
2011/0069292 A1    3/2011 Den Boef
2012/0218547 A1    8/2012 Konradi et al.
2015/0077764 A1*  3/2015 Braker ............... G01B 11/2518
                                                      356/620

* cited by examiner

SYSTEM AND METHOD FOR HYPERSPECTRAL IMAGING METROLOGY

CROSS-REFERENCE TO RELATED APPLICATION

The present application claims the benefit under 35 U.S.C. § 119(e) of U.S. Provisional Application Ser. No. 62/290,157, filed Feb. 2, 2016, entitled HYPER SPECTRAL IMAGING IN OVERLAY SCATTEROMETRY, naming Andrew V. Hill as inventor, which is incorporated herein by reference in the entirety.

The present application claims the benefit under 35 U.S.C. § 119(e) of U.S. Provisional Application Ser. No. 62/365,120, filed Jul. 21, 2016, entitled SYSTEM AND METHOD FOR HYPERSPECTRAL IMAGING METROLOGY, naming Andrew V. Hill as inventor, which is incorporated herein by reference in the entirety.

TECHNICAL FIELD

The present disclosure relates generally to metrology, and, more particularly, to hyperspectral imaging metrology.

BACKGROUND

Scatterometry metrology systems may characterize the size, shape, or distribution of features on a semiconductor wafer by measuring and analyzing a pattern of optical radiation (e.g. light) scattered, reflected, or diffracted from the sample instead of and/or in addition to measuring an image of the sample. The pattern of scattered, reflected, or diffracted light detected by metrology system may be influenced by the specific features on the wafer as well as the wavelengths of light incident on the wafer. Accordingly, a sensitivity of this pattern of scattered, reflected, or diffracted light from a particular wafer may vary based on the incident wavelengths of light.

It may be desirable to characterize a wafer with multiple wavelengths of light. However, typical approaches for generating multiple scatterometry measurements increase measurement acquisition time relative to a single measurement and/or decrease the light associated with each measurement. Therefore, it would be desirable to provide a system and method for curing defects such as those of the identified above.

SUMMARY

A metrology system is disclosed in accordance with one or more illustrative embodiments of the present disclosure. In one illustrative embodiment, the metrology system includes an illumination source configured to generate an illumination beam. In another illustrative embodiment, the metrology system includes one or more illumination optics configured to direct the illumination beam to a sample. In another illustrative embodiment, the metrology system includes one or more collection optics configured to collect illumination emanating from the sample. In another illustrative embodiment, the metrology system includes a detector. In another illustrative embodiment, the metrology system includes a hyperspectral imaging sub-system. In another illustrative embodiment, the hyperspectral imaging sub-system includes a dispersive element positioned at a pupil plane of the set of collection optics configured to spectrally disperse the collected illumination. In another illustrative embodiment, the hyperspectral imaging sub-system includes a lens array including an array of focusing elements. In another illustrative embodiment, the hyperspectral imaging sub-system includes one or more imaging optics. In another illustrative embodiment, the one or more imaging optics combine the spectrally-dispersed collected illumination to form an image of the pupil plane on the lens array. In another illustrative embodiment, the focusing elements of the lens array distribute the collected illumination on the detector in an arrayed pattern.

A hyperspectral imaging apparatus is disclosed in accordance with one or more illustrative embodiments of the present disclosure. In one illustrative embodiment, the hyperspectral imaging apparatus includes a dispersive element configured to be positioned at a pupil plane of a set of collection optics. In another illustrative embodiment, the set of collection optics are configured to collect illumination emanating from a sample. In another illustrative embodiment, the dispersive element is configured to spectrally disperse the collected illumination. In another illustrative embodiment, the hyperspectral imaging apparatus includes a lens array including an array of focusing elements. In another illustrative embodiment, the hyperspectral imaging apparatus includes one or more imaging optics. In another illustrative embodiment, the one or more imaging optics combine the spatially-dispersed set of wavelengths to image the pupil plane on the lens array. In another illustrative embodiment, the focusing elements of the lens array are configured to distribute the collected illumination in an arrayed pattern.

A method is disclosed, in accordance with one or more illustrative embodiments of the present disclosure. In one illustrative embodiment, the method includes collecting illumination from a sample by a set of collection optics. In another illustrative embodiment, the method includes spectrally dispersing the collected illumination by a dispersing element, wherein the dispersing element is positioned at a pupil plane of the set of collection optics. In another illustrative embodiment, the method includes generating an image of the pupil plane on a lens array including an array of focusing elements. In another illustrative embodiment, the spectrally-dispersed set collected illumination is combined to form the image of the pupil plane. In another illustrative embodiment, the method includes distributing the collected illumination in an arrayed pattern.

BRIEF DESCRIPTION OF DRAWINGS

The numerous advantages of the disclosure may be better understood by those skilled in the art by reference to the accompanying figures in which.

DETAILED DESCRIPTION

Figure 1:
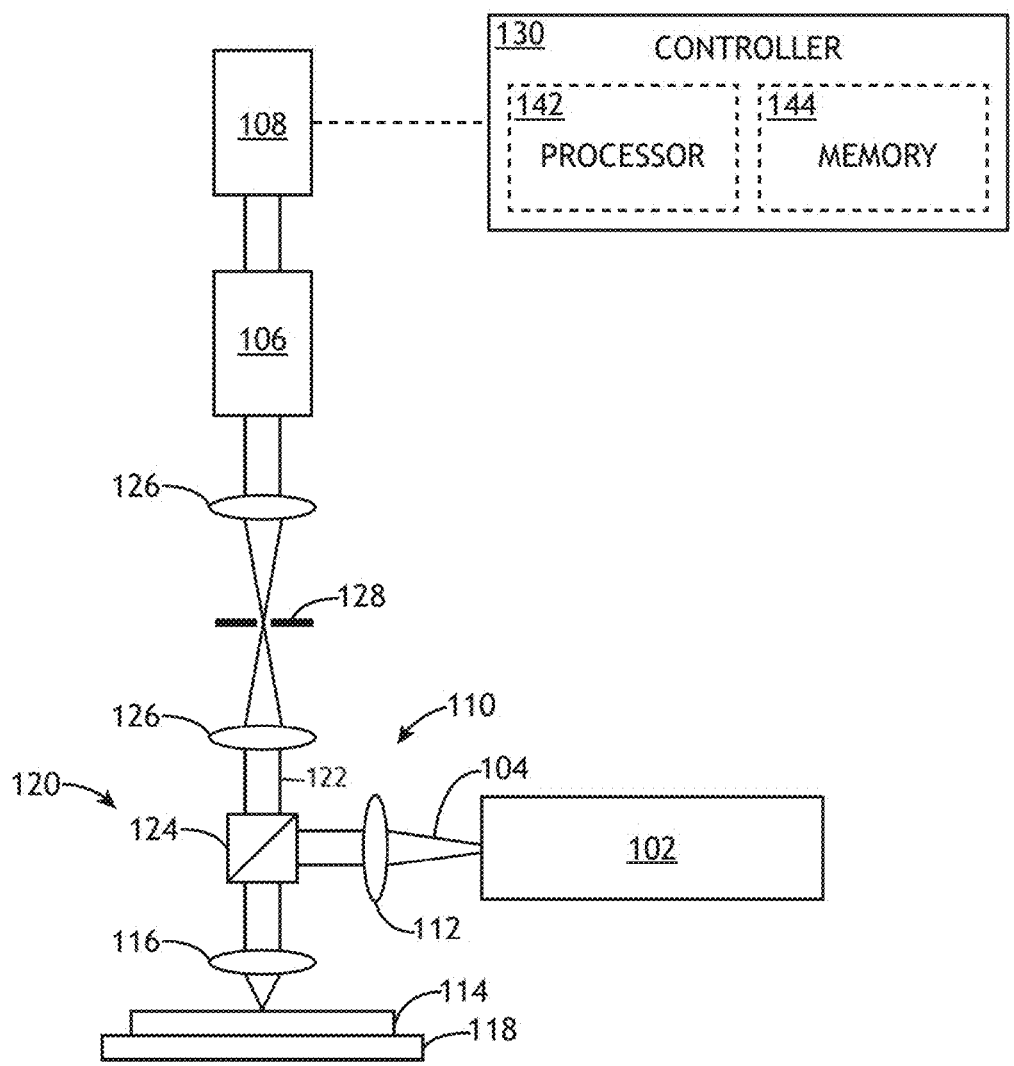
FIG. 1 is a conceptual view of a hyperspectral metrology system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 6, systems and methods for hyperspectral imaging metrology are disclosed, in accordance with one or more embodiments of the present disclosure. Embodiments of the present disclosure are directed to a hyperspectral metrology system for simultaneously measuring multiple metrology images associated with multiple wavelengths on a single detector. Additional embodiments of the present disclosure are directed to measuring spectrally-resolved illumination associated with a pupil plane of the metrology system (e.g. a back focal plane of an objective lens, a diffraction plane, or the like). Further embodiments are directed to interleaving illumination associated with the pupil plane for multiple wavelengths to facilitate simultaneous measurement of spectrally resolved illumination associated with the angular distribution of light from a sample.

It is recognized herein that scatterometry metrology systems may typically characterize one or more aspects of a sample by measuring and analyzing a pattern of scattered, reflected, or diffracted light from the sample. Further, the pattern of scattered, reflected, or diffracted light may be measured instead of and/or in addition to an image of the sample. It is noted that optical systems typically include two reciprocal planes: an image plane and a pupil plane. An image plane (e.g. a field plane or any plane conjugate to the image plane) may correspond to an image of the sample. Accordingly, light emanating from a particular point on the sample at any angle may be imaged to a corresponding particular point in the image plane. Conversely, light emanating from the sample at a particular angle, regardless of the location on the sample, may be imaged to a particular point in the pupil plane (or any plane conjugate to the pupil plane). In this regard, a spatial distribution of light in the pupil plane may correspond to an angular distribution of light collected from the sample.

It is further recognized that the pupil plane may correspond to the back focal plane of an optical element collecting light from the sample (e.g. an objective lens, or the like). For example, many objective lenses provide an aperture stop at the back focal plane (e.g. corresponding to the pupil plane) such that the angular extent, or the numerical aperture, of light propagating through the system is limited in this diffraction plane. For the purposes of the present disclosure, the terms pupil plane, back focal plane, and diffraction plane are used interchangeably. It is noted, however, that the description of the location of the pupil plane, the back focal plane, and diffraction planes above are provided solely for illustrative purposes and should not be interpreted as limiting.

Additionally, a distribution of light in a pupil plane may vary according to the wavelength of illumination. For example, features on a sample may scatter, reflect, and/or diffract illumination including a first wavelength in a first angular distribution and may further scatter, reflect, and/or diffract illumination including a second wavelength in a second angular distribution. It is recognized that a distribution pattern of radiation in a pupil plane (e.g. a scatterometry signal) associated with illumination including certain wavelengths may be more sensitive than others to deviations of sample characteristics (e.g. a size, shape, or distribution of features on a sample). Accordingly, it may be beneficial to simultaneously measure illumination associated with a pupil plane for multiple wavelengths. Embodiments of the present disclosure are directed to a hyperspectral imaging system to measure spectrally resolved illumination associated with the pupil plane of a metrology system. Some embodiments of the present disclosure are directed to dividing the pupil plane into multiple segments and directing spectrally-dispersed illumination from each segment onto a detector. In this regard, data associated with illumination from the pupil plane for multiple wavelengths may be simultaneously measured. Some embodiments of the present disclosure are directed to generating a scaled and spectrally-dispersed image of each of the segments on a detector. Accordingly, images of the pupil plane for multiple wavelengths may be simultaneously measured.

As used throughout the present disclosure, the term "sample" generally refers to a substrate formed of a semiconductor or non-semiconductor material (e.g. a wafer, or the like). For example, a semiconductor or non-semiconductor material may include, but is not limited to, monocrystalline silicon, gallium arsenide, and indium phosphide. A sample may include one or more layers. For example, such layers may include, but are not limited to, a resist, a dielectric material, a conductive material, and a semiconductive material. Many different types of such layers are known in the art, and the term sample as used herein is intended to encompass a sample on which all types of such layers may be formed. One or more layers formed on a sample may be patterned or unpatterned. For example, a sample may include a plurality of dies, each having repeatable patterned features. Formation and processing of such layers of material may ultimately result in completed devices. Many different types of devices may be formed on a sample, and the term sample as used herein is intended to encompass a sample on which any type of device known in the art is being fabricated. Further, for the purposes of the present disclosure, the term sample and wafer should be interpreted as interchangeable.

FIG. 1 is a conceptual view of a hyperspectral metrology system, in accordance with one or more embodiments of the present disclosure. In one embodiment, the system 100 includes an illumination source 102 configured to generate an illumination beam 104 having spectral content including multiple wavelengths, a hyperspectral imaging sub-system 106 located at a pupil plane of the system 100 to spectrally disperse illumination at the pupil plane, and a detector 108 to capture spectrally dispersed illumination associated with the pupil plane. In this regard, the system 100 may simultaneously capture illumination associated with the pupil plane for multiple discrete spectral bands.

In another embodiment, the illumination source 102 may include, but is not limited to, a polychromatic light source with a spectrum including multiple discrete wavelengths, a broadband light source, a wavelength-tunable light source, or a wavelength-sweeping light source. Further, the spectral content of the illumination beam 104 may include selected wavelengths of light including, but not limited to, ultraviolet (UV) radiation, visible radiation, or infrared (IR) radiation. In another embodiment, the illumination source 102 includes a supercontinuum laser source.

In another embodiment, the system 100 includes an illumination pathway 110 including one or more illumination optical elements 112 to direct the illumination beam 104 to a sample 114. The illumination optical elements 112 may include one or more optical elements suitable for modifying and/or conditioning the illumination beam 104. For example, the illumination pathway 110 may include an objective lens 116 to focus the illumination beam 104 onto one or more locations on the sample 114. In another embodiment, the system 100 includes a stage assembly 118 suitable for securing a sample 114. Further, the stage assembly 118 may position and/or translate the sample 114 to expose one or more portions of the sample 114 to the illumination beam 104.

In another embodiment, the system 100 includes a collection pathway 120 including one or more optical elements to collect sample radiation 122 emanating from the sample 114. For example, the collection pathway 120 may receive radiation reflected or scattered (e.g. via specular reflection, diffuse reflection, and the like) from the sample 114. By way of another example, the collection pathway 120 may receive radiation generated by the sample 114 (e.g. luminescence associated with absorption of the illumination beam 104, and the like). As an additional example, the collection pathway 120 may receive one or more diffracted orders of radiation from the sample 114 (e.g. 0-order diffraction, ±1 order diffraction, ±2 order diffraction, and the like).

The system 100 may include, but is not required to include, a beamsplitter 124 as part of both the illumination pathway 110 and/or the collection pathway 120. In this regard, a single optical element (e.g. objective lens 116) may direct the illumination beam 104 along a first optical path through the beamsplitter 124 to the sample 114 and direct sample radiation 122 from the sample 114 along a second optical path through the beamsplitter 124.

In another embodiment, the system 100 includes one or more relay optical elements 126. For example, the relay optical elements 126 may relay the pupil plane or a plane conjugate to the pupil plane to the hyperspectral imaging sub-system 106 (e.g. to a first optical element of the hyperspectral imaging sub-system 106, to an entrance pupil of the hyperspectral imaging sub-system 106, or the like). For example, the relay optical elements 126 may generate an image of a pupil plane (e.g. a back aperture of the objective lens 116, a diffraction plane, or the like) on a first optical element of the hyperspectral imaging sub-system 106. Accordingly, the hyperspectral imaging sub-system 106 may spectrally disperse the distribution of sample radiation 122 at the pupil plane and direct the radiation to the detector 108 for the simultaneous capture of illumination associated with the pupil plane for multiple wavelengths of the sample radiation 122. In another embodiment, the system 100 includes a field stop 128 to limit the field of view of the sample 114 propagating through the system 100.

In another embodiment, the system 100 includes a controller 130 communicatively coupled to the detector 108. For example, the controller 130 may be configured to receive data including, but not limited to, measurement results, (images of the target, pupil images, and the like) or metrology metrics (e.g. precision, tool-induced shift, sensitivity, diffraction efficiency, through-focus slope, side wall angle, critical dimensions, and the like). In another embodiment, the controller 130 is communicatively coupled to the illumination source 102. For example, the controller 130 may direct the illumination source 102 to provide one or more selected wavelengths of illumination. In a general sense, the controller 130 may be communicatively coupled with any element within the system 100. In another embodiment, the controller 130 is communicatively coupled to the illumination optical elements 112 and/or the illumination source 102 to direct the adjustment of the angle of incidence between the illumination beam 104 and the sample 114.

In another embodiment, the controller 130 performs data analysis on data received from the detector 108. For example, the controller 130 may generate metrology data (e.g. overlay metrology data, scatterometry data, or the like) based on data received from the detector 108.

Figure 2:
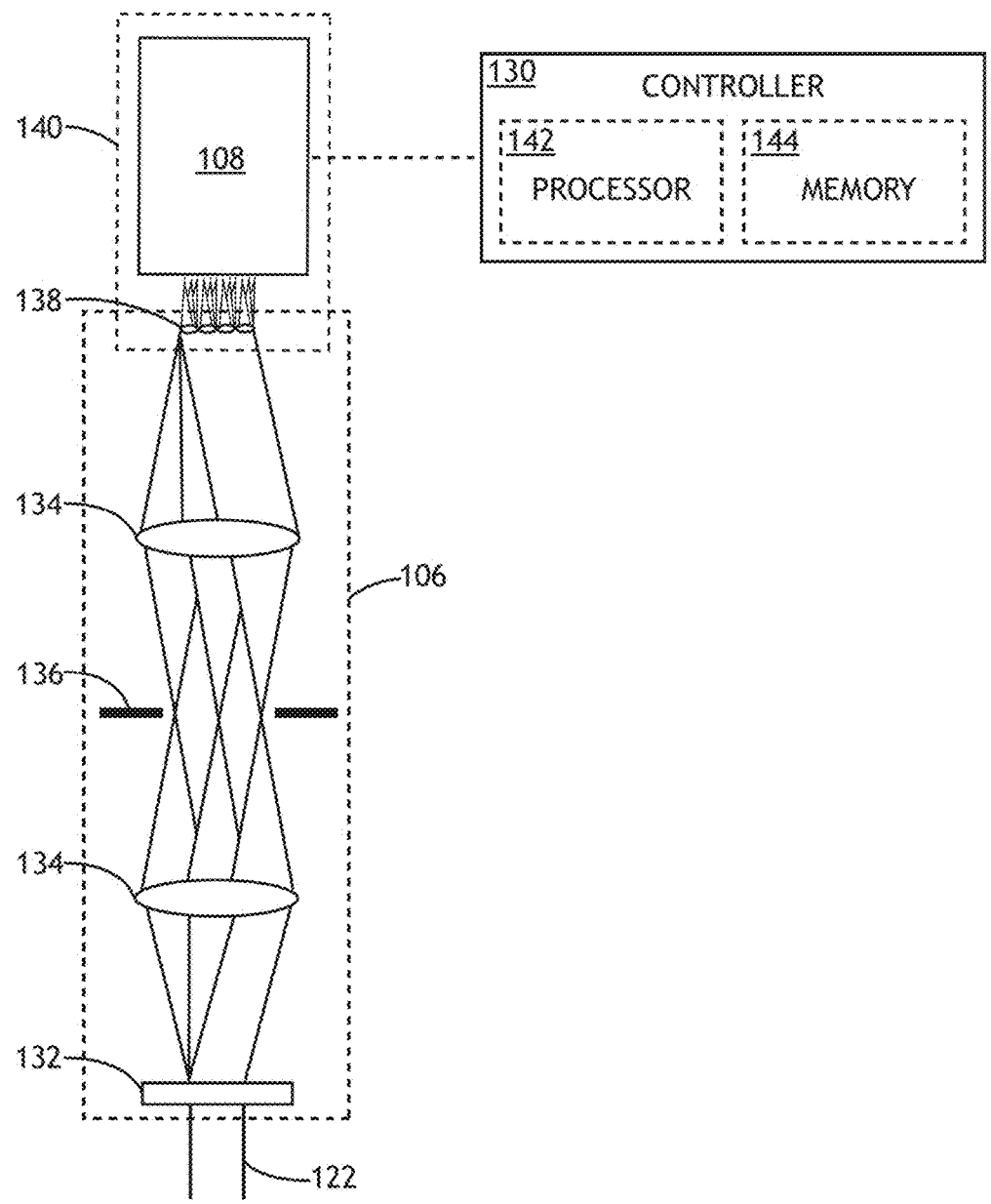
FIG. 2 is a conceptual view of a hyperspectral metrology system including an expanded view of the hyperspectral imaging sub-system, in accordance with one or more embodiments of the present disclosure.

FIG. 2 is a conceptual view of a hyperspectral metrology system including an expanded view of the hyperspectral imaging sub-system 106, in accordance with one or more embodiments of the present disclosure. In one embodiment, the hyperspectral imaging sub-system 106 spectrally disperses the sample radiation 122 at the pupil plane, divides the pupil plane into multiple segments and directs illumination associated with each segment to spatially separated portions of the detector 108. In this regard, illumination associated with the pupil plane may be segmented and distributed as an array pattern on the detector 108. In another embodiment, the hyperspectral imaging sub-system 106 spectrally disperses the sample radiation 122 on the detector 108 such that the array pattern is spectrally dispersed. Accordingly, illumination associated with the pupil plane having different wavelengths may occupy different locations on the detector.

In one embodiment, the hyperspectral imaging sub-system 106 includes a dispersive element 132 located at a pupil plane of the system 100 to spectrally disperse the distribution of sample radiation 122 at the pupil plane. For example, the dispersive element 132 may disperse the sample radiation 122 at the pupil plane such that the exit angle of sample radiation 122 from the dispersive element 132 varies according to spectral content (e.g. wavelength). By way of illustration, as shown in FIG. 2, sample radiation 122 including three distinct wavelengths incident on the dispersive element 132 may be dispersed into distinct sub-beams of sample radiation 122 (e.g. $\lambda_1, \lambda_2, \lambda_3$).

It is noted, however, that the depiction of sub-beams associated with distinct wavelengths illustrated in FIG. 2 and described above is provided solely for illustrative purposes and should not be interpreted as limiting. For example, the sample radiation 122 may include a broad spectral range (e.g. associated with the spectral range of the illumination beam 104, or the like) such that the sample radiation 122 dispersed by the dispersive element 132 may include a single spectrally-dispersed beam (e.g. without distinct sub-beams).

The dispersive element 132 may be any type of dispersive element known in the art suitable for introducing spectral dispersion into the sample radiation 122. For example, dispersive element 132 may introduce dispersion into the sample radiation 122 through any mechanism such as, but not limited to, diffraction or refraction. Further, the dispersive element 132 may be formed from transmissive and/or reflective optical elements.

In one embodiment, the dispersive element 132 includes a prism to spectrally disperse the sample radiation 122 by refracting the sample radiation 122 at different angles according to spectral content (e.g. wavelength). In another embodiment, the dispersive element 132 includes a diffractive optical element to spectrally disperse the sample radiation 122 through diffraction. For example, the dispersive element 132 may include a diffraction grating to spectrally disperse the sample radiation 122 in the pupil plane such that the diffraction angle varies according to the spectral content of the sample radiation 122. A dispersive element 132 may include any type of diffraction grating such as, but not limited to, a fabricated grating (e.g. a holographic grating, a ruled grating, a blazed grating, or the like), or a dynamically generated grating (e.g. an acousto-optic modulator, an electro-optical modulator, or the like). In one embodiment, the dispersive element 132 includes an acousto-optic modulator consisting of a solid medium coupled with a transducer configured to generate ultrasonic waves that propagate through the solid medium. Properties of the solid medium such as, but not limited to, the refractive index may be modified by the propagating ultrasonic waves such that the sample radiation 122 is diffracted upon interaction with the solid medium. Furthermore, ultrasonic waves may propagate through the solid medium at the velocity of sound in the medium and have a wavelength related to the frequency of the drive signal as well as the velocity of sound in the solid medium.

In another embodiment, the hyperspectral imaging sub-system 106 includes hyperspectral relay optical elements 134 to relay the pupil plane (e.g. relay an image of the pupil plane located at the first optical element of the hyperspectral imaging sub-system 106, the entrance pupil of the hyperspectral imaging sub-system 106, or the like). For example, as illustrated in FIG. 2, the hyperspectral relay optical elements 134 may collect at least a portion of the spectrally-dispersed sample radiation 122 directed from the dispersive element 132 to form the relayed image of the pupil plane. In this regard, the hyperspectral relay optical elements 134 may combine the spectrally-dispersed components of the sample radiation 122 to form the image of the pupil plane. Accordingly, the sample radiation 122 may not be spectrally dispersed at the location of the relayed image of the pupil plane, but may be spectrally dispersed elsewhere within the hyperspectral imaging sub-system 106.

The hyperspectral imaging sub-system 106 may include a plane conjugate to the sample 114 (e.g. a field plane) located between two of the hyperspectral relay optical elements 134 in containing a spectrally-dispersed image of the sample 114. In one embodiment, the hyperspectral imaging sub-system 106 includes a filter (e.g. a spatial filter to limit the spectral content of the sample radiation 122). For example, the hyperspectral imaging sub-system 106 may include a spectral field stop 136 to limit the spectral extent of the sample radiation 122. By way of another example, the hyperspectral imaging sub-system 106 may include a partially-transmissive element to selectively control the intensity of each portion of the spectral content of the sample radiation 122. For example, the intensity of portions of the spectral content of the sample radiation 122 may be normalized to a common value to compensate for differences in diffraction efficiency of a diffractive dispersive element 132. By way of another example, the hyperspectral imaging sub-system 106 may include a dynamically controllable element, such as, but not limited to, a spatial light modulator, to dynamically control the spectral content of the sample radiation 122 propagating to the detector 108.

In another embodiment, the hyperspectral imaging sub-system 106 includes a lens array 138 formed as an array of focusing elements (e.g. lenses). In another embodiment, the lens array 138 is located at the relayed image of the pupil plane such that the lens array 138 divides the sample radiation 122 in the pupil plane into multiple segments according to the distribution of focusing elements of the lens array 138. In this regard, each focusing element of the lens array 138 may capture a particular portion of the distribution of sample radiation 122 in the pupil plane.

Figure 3:
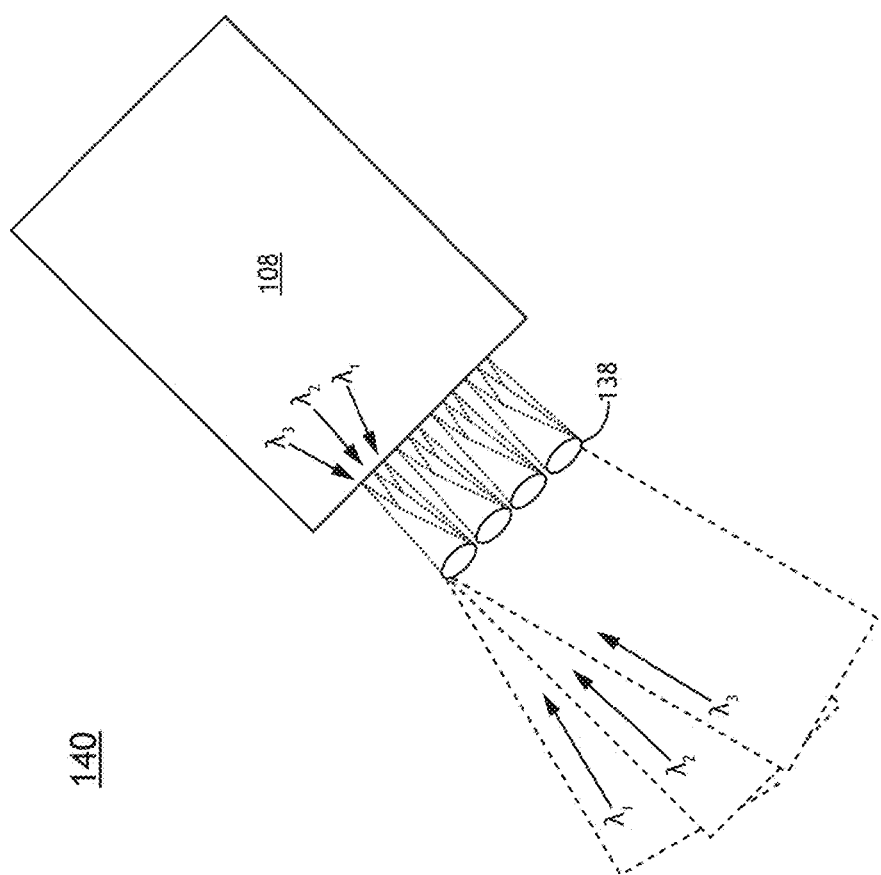
FIG. 3 is an expanded view of a portion of FIG. 2 illustrating the segmentation of sample radiation in the pupil plane by lens array, in accordance with one or more embodiments of the present disclosure.

FIG. 3 is an expanded view of a portion 140 of FIG. 2 illustrating the segmentation of sample radiation 122 in the pupil plane by lens array 138, in accordance with one or more embodiments of the present disclosure. In one embodiment, the incidence angle of the sample radiation 122 on the lens array 138 varies according to the spectral content (e.g. the wavelength). Further, the exit angle of the sample radiation 122 from the lens array 138 may vary according to the spectral content (e.g. the wavelength). In this regard, each focusing element of the lens array 138 may collect illumination associated with all wavelengths from a particular portion of the pupil plane (e.g. associated with a particular range of scattering angles from the sample 114) and direct the collected illumination to the detector 108 in a spectrally dispersed pattern.

In another embodiment, each focusing element of the lens array 138 focuses the sample radiation 122 onto the detector 108. For example, as illustrated in FIG. 3, the lens array 138 may focus the sample radiation 122 such that sample radiation 122 collected by adjacent focusing elements does not overlap on the detector 108.

The size, shape, or distribution of focusing elements of the lens array 138 may control the segmentation of the pupil plane (e.g. the range of scattering angles of sample radiation 122 collected by each focusing element) as well as the distribution of sample radiation 122 on the detector. The lens array 138 may be any type of lens array known in the art such as, but not limited to, a one-dimensional lens array or a two-dimensional lens array. In one embodiment, the lens array 138 includes a one-dimensional lens array. For example, a one-dimensional lens array may be formed as a one-dimensional array of cylindrical lenses. In another embodiment, the lens array 138 includes a two-dimensional lens array. For example, a two-dimensional lens array may include focusing elements distributed in a two-dimensional pattern such as, but not limited to, a grid pattern, an offset grid pattern, or a hexagonal pattern. Further, focusing elements may be distributed in a regular pattern (e.g. a lattice arrangement, or the like) or an irregular pattern. Additionally, focusing elements may be distributed in a periodic arrangement or a non-periodic arrangement (e.g. a random arrangement, or the like).

It is noted herein that the range of scattering angles of sample radiation 122 collected by a particular focusing element of a lens array 138 located at a pupil plane of the system 100 may depend on the size or shape of the particular focusing element. In one embodiment, the size of the focusing elements of the lens array 138 is constant across the spatial extent of the image of the pupil plane. In this regard, a size of a range of scattering angles of sample radiation 122 collected by each focusing element may be constant. In another embodiment, the size of the focusing elements of the lens array 138 may vary across the extent of the image of the pupil plane. For example, the size of focusing elements may be smaller in regions of interest of the pupil plane relative to additional regions such that the resolution of captured scattering angles may be increased in the regions of interest.

The lens array 138 may include refractive and/or diffractive optical elements. For example, lens array 138 may include, but are not limited to, spherical focusing elements (e.g. focusing elements in which one or more surfaces include a portion of a sphere), Fresnel focusing elements, or diffractive optical elements embedded as regions of varying index of refraction within a volume of a transparent material.

Figure 4:
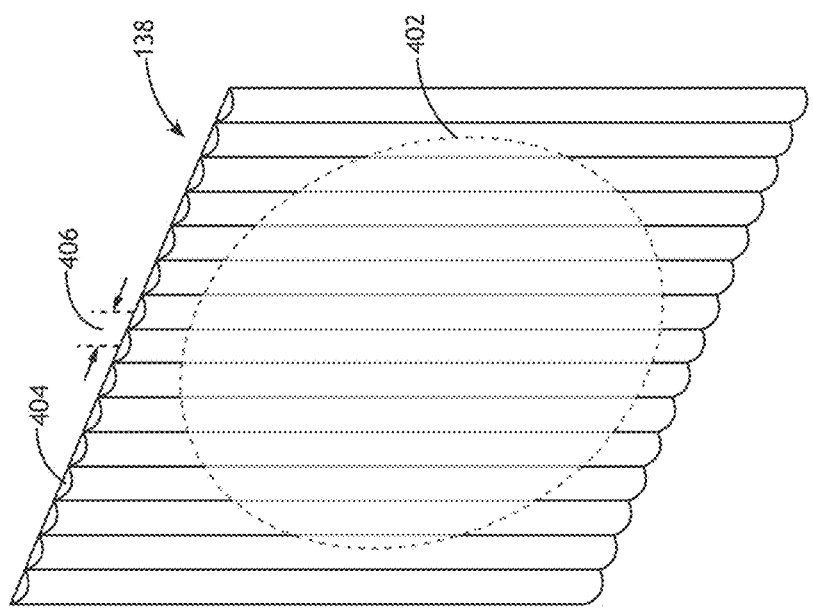
FIG. 4 is a schematic view illustrating the formation of an image of the pupil plane on a lens array, in accordance with one or more embodiments of the present disclosure.

FIG. 4 is a schematic view illustrating the formation of an image of the pupil plane 402 on lens array 138, in accordance with one or more embodiments of the present disclosure. In one embodiment, the lens array 138 includes a one-dimensional array of cylindrical focusing elements 404. For example, as illustrated in FIG. 4, a lens array 138 may include an array of adjacent cylindrical focusing elements 404 having equal width distributed with pitch 406. In this regard, the lens array 138 may divide the image of the pupil plane 402 into a series of linear segments. Accordingly, each linear segment of the image of the pupil plane 402 may include sample radiation 122 scattered by the sample 114 within a range of scattering angles as measured along the direction of separation of the focusing elements. Further, the image of the pupil plane 402 may not be segmented along a second direction perpendicular to the first direction.

Figure 5:
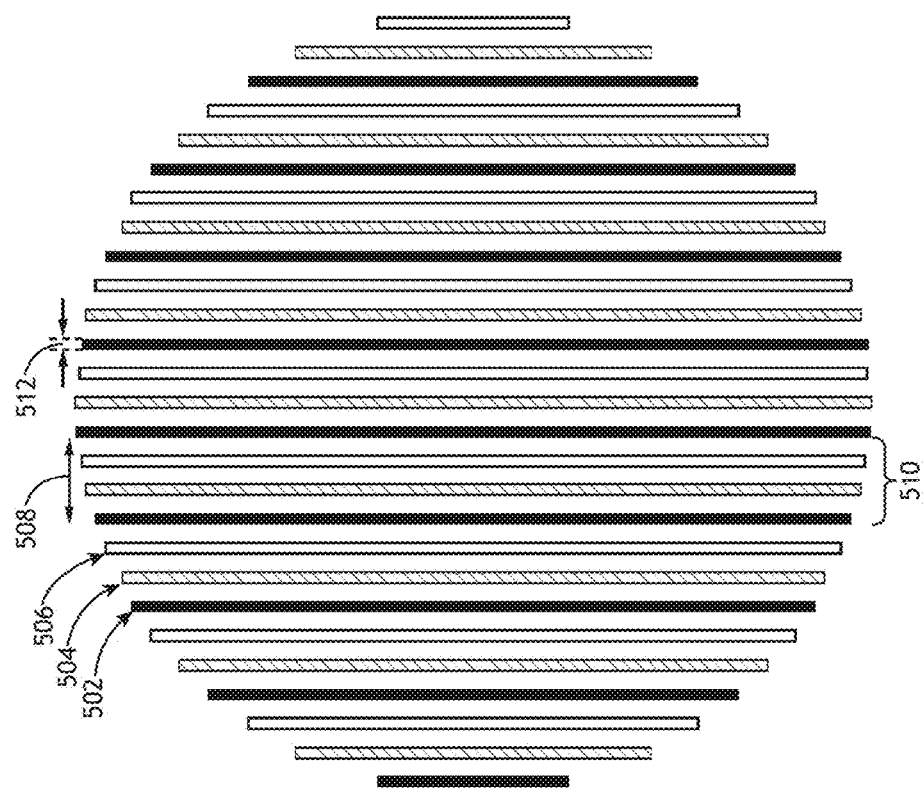
FIG. 5 is a schematic view illustrating an exemplary distribution of sample radiation on a detector by the lens array illustrated in FIG. 4, in accordance with one or more embodiments of the present disclosure.

FIG. 5 is a schematic view illustrating an exemplary distribution of sample radiation 122 on a detector 108 formed by the lens array 138 as depicted in FIG. 4, in accordance with one or more embodiments of the present disclosure. In one embodiment, sample radiation 122 including three distinct wavelengths (e.g. $\lambda_1$, $\lambda_2$, $\lambda_3$) is spectrally dispersed across the detector 108. For example, sample radiation 122 associated with wavelength $\lambda_1$ in the image of the pupil plane 402 may be segmented and focused onto the detector 108 as an array pattern 502. In this regard, each segment of the array pattern 502 may include sample radiation 122 associated with a particular range of scattering angles from the sample 114. Further, sample radiation 122 associated with wavelength $\lambda_2$ in the image of the pupil plane 402 may be segmented and focused onto the detector 108 as an array pattern 504, which is displaced (e.g. offset, or the like) from the array pattern 502. Additionally, sample radiation 122 associated with wavelength $\lambda_3$ in the image of the pupil plane 402 may be segmented and focused onto the detector 108 as an array pattern 506, which is further displaced from the array pattern 502. In this regard, the array patterns 502,504,506 may be interleaved on the detector 108. In another embodiment, as illustrated in FIG. 5, the spectral ranges of sample radiation 122 are distributed on the detector 108 in a non-overlapping distribution. For example, each of the array patterns 502,504,506 may have a pitch 508 and may be displaced relative to each other. Further, a spatial extent 510 of the spectrally dispersed sample radiation 122 on the detector 108 (e.g. a spatial extent of illumination of all spectrally-dispersed wavelengths from a single focusing element of the lens array 138) may be smaller than the pitch 508. In this regard, illumination from adjacent focusing elements may not overlap on the detector 108.

It is noted herein that the description of distinct array patterns on the detector 108 illustrated in FIG. 5 as well as the associated description are provided solely for illustrative purposes and should not be interpreted as limiting. For example, sample radiation 122 may be distributed as a single spectrally-dispersed array pattern. Further, in the case that the spectral content of the sample radiation 122 includes a continuous range of wavelengths (e.g. associated with a broadband illumination source 102, or the like), the spatial extent 510 of the spectrally-dispersed sample radiation 122 may include a corresponding continuously-varying distribution of wavelengths of the sample radiation 122.

It is further noted that the distribution of sample radiation 122 on the detector 108 may be controlled by the shape, size, or distribution of the focusing elements of the lens array 138. For example, as illustrated in FIG. 5, a lens array 138 formed from a one-dimensional array of cylindrical lenses may provide a linear array pattern (e.g. array pattern 502) on the detector 108. By way of another example, a lens array 138 formed from a two-dimensional array of focusing elements may provide a two-dimensional array pattern on the detector 108. In some embodiments, a two-dimensional lens array 138 may be coupled with a two-dimensional dispersive element 132 such that the sample radiation 122 is spectrally dispersed in two-dimensions on the detector 108.

In another embodiment, the detector 108 may be placed at a focal plane of the lens array 138. In this regard, a width 512 of a segment of an array pattern associated with a particular wavelength of sample radiation 122 collected by a focusing element may be related to a field of view of the sample 114 as captured by the system 100. Further, the width 512 may be controllable by a field stop (e.g. field stop 128 of FIG. 1, or the like). Accordingly, the width 512 may be adjusted to mitigate overlap of spectral content of the sample radiation 122 (e.g. distinct spectral ranges, a continuous spectral distribution, or the like).

In another embodiment, sample radiation 122 collected by each focusing element of the lens array 138 is provided to the detector 108 as a scaled image of the corresponding portion of the pupil plane. For example, the hyperspectral relay optical elements 134, the lens array 138, and/or one or more additional optical elements (not shown) may relay segmented and spatially dispersed representation of the pupil plane to the detector 108. By way of another example, one or more additional relay optical elements (not shown) may relay the pupil plane from the lens array 138 to the detector 108. In this regard, the detector 108 may simultaneously capture multiple segmented, scaled, and interleaved instances of the pupil plane (e.g. corresponding to multiple spectral ranges of the sample radiation 122).

In another embodiment, a pupil image representative of the angular distribution of light of a particular spectral range emanating from the sample may be constructed by considering the pixels of the detector 108 receiving the array pattern of the particular spectral range. For example, a pupil image may include multiple segments in an array pattern in which each segment includes focused illumination from a portion of the pupil plane. By way of another example, a pupil image may include multiple segments in an array pattern in which each segment includes a scaled image of a portion of the pupil plane. In another embodiment, the array patterns of multiple pupil images may be interleaved on the detector. In this regard, the detector 108 may simultaneously capture more than one pupil image in which each pupil image represents a different spectral range of illumination from the sample.

In another embodiment, measured data from the detector 108 may be processed (e.g. by the controller 130, or the like) to merge and/or scale the segments of the measured array pattern to form a continuous pupil image.

It is noted herein that segmenting the sample radiation 122 in the pupil plane and directing spectrally-dispersed sample radiation 122 from each segment to a detector may provide an efficient use of light, physical space and/or measurement time of the system 100. For example, the optical intensity at each wavelength of collected sample radiation 122 (e.g. the spectral power) may be provided to the detector with minimal loss. By way of another example, spectrally-resolved illumination associated with the pupil plane may be measured by a single detector 108 using the same detector area required to measure a single image of the pupil plane. For instance, segmenting the pupil plane (e.g. by the lens array 138, or the like) and focusing the sample radiation 122 from each segment onto the detector 108 may reduce the detector area required for each wavelength of sample radiation 122 and may provide space on the detector 108 for the simultaneous capture of illumination associated with the pupil plane for multiple wavelengths. Further, simultaneously measuring spectrally resolved illumination associated with the pupil plane may facilitate fast measurement times (e.g. relative to sequentially capturing images of the pupil plane for different illumination wavelengths, or the like).

Referring again to FIG. 1, the illumination source 102 may include any illumination source known in the art suitable for generating an illumination beam 104 with multiple spectral components. For example, the illumination source 102 may include a broad spectral range for the simultaneous capture of illumination associated with the pupil plane for a broad spectrum of wavelengths. By way of another example, the illumination source 102 may include multiple ranges of narrow spectral bands for the simultaneous capture of illumination associated with the pupil plane for the selected spectral bands of illumination.

The illumination source 102 may be, but is not limited to be, formed from a white light source (e.g. a broadband light source with a spectrum including visible wavelengths), a laser source, an arc lamp, an electrode-less lamp, or a laser sustained plasma (LSP) source. For example, the illumination source 102 may include a supercontinuum light source. As another example, the illumination source 102 may include a supercontinuum laser source (e.g. a white light laser source). Further, the illumination beam 104 may be delivered via free-space propagation or guided light (e.g. an optical fiber, a light pipe, or the like). In another embodiment, the illumination source 102 is a tunable illumination source. In this regard, the wavelengths of radiation of the illumination beam 104 may be adjusted to any selected wavelength of radiation (e.g. UV radiation, visible radiation, infrared radiation, or the like). Additionally, the illumination beam 104 may exhibit any degree of spatial and/or temporal coherence. For example, an illumination source 102 configured as a laser source may generate a spatially and temporally coherent illumination beam 104. By way of another example, an illumination source 102 configured as a lamp source may generate a spatially and/or temporally incoherent illumination beam 104.

The illumination source 102 may direct the illumination beam 104 to the sample 114 at any angle via the illumination pathway 110. For example, the illumination optical elements 112 may include, but are not limited to, one or more lenses, one or more polarizers, one or more filters, one or more beam splitters, one or more diffusers, one or more homogenizers, one or more apodizers, or one or more beam shapers. In one embodiment, the illumination source 102 directs the illumination beam 104 to the sample 114 at normal incidence angle to a surface of the sample 114. In another embodiment, the illumination source 102 directs the illumination beam 104 to the sample 114 at an angle (e.g. a glancing angle, a 45-degree angle, and the like). In another embodiment, the angle of incidence of the illumination beam 104 on the sample 114 is adjustable. For example, the path of the illumination beam 104 through the beamsplitter 124 and the objective lens 116 may be adjusted to control the angle of incidence of the illumination beam 104 on the sample 114. In this regard, the illumination beam 104 may have a nominal path through the beamsplitter 124 and the objective lens 116 such that the illumination beam 104 has a normal incidence angle on the sample 114. Further, the angle of incidence of the illumination beam 104 on the sample 114 may be controlled by modifying the position and/or angle of the illumination beam 104 on the beamsplitter 124 (e.g. by rotatable mirrors, a spatial light modulator, a free-form illumination source, or the like).

The stage assembly 118 may include any sample stage architecture known in the art. For example, the stage assembly 118 may include, but is not limited to, a linear stage. By way of another example, the stage assembly 118 may include, but is not limited to, a rotational stage. Further, the sample 114 may include a wafer, such as, but not limited to, a semiconductor wafer.

Further, it is noted herein that the detector 108 may include any optical detector known in the art suitable for measuring illumination received from the sample 114. For example, a detector 108 may include, but is not limited to, a CCD detector, a TDI detector, a photomultiplier tube (PMT), an avalanche photodiode (APD), or the like. In another embodiment, a detector 108 may include a spectroscopic detector suitable for identifying wavelengths of radiation emanating from the sample 114. Further, the collection pathway 120 may include multiple optical elements to direct and/or modify illumination collected by the objective lens 116 including, but not limited to, one or more lenses, one or more filters, one or more polarizers, one or more beam blocks, or one or more beamsplitters.

In another embodiment, the controller 130 includes one or more processors 142. In another embodiment, the one or more processors 142 are configured to execute a set of program instructions maintained in a memory 144, or memory medium. Further, the controller 130 may include one or more modules containing one or more program instructions stored in the memory 144 executable by the one or more processors 142. The one or more processors 142 of a controller 130 may include any processing element known in the art. In this sense, the one or more processors 142 may include any microprocessor-type device configured to execute algorithms and/or instructions. In one embodiment, the one or more processors 142 may consist of a desktop computer, mainframe computer system, workstation, image computer, parallel processor, or any other computer system (e.g., networked computer) configured to execute a program configured to operate the system 100, as described throughout the present disclosure. It is further recognized that the term "processor" may be broadly defined to encompass any device having one or more processing elements, which execute program instructions from a non-transitory memory 144.

It is recognized herein that the steps described throughout the present disclosure may be carried out by the controller 130. Further, the controller 130 may be formed from a single component or multiple components. It is further noted herein that the multiple components of the controller 130 may be housed in a common housing or within multiple housings. In this way, any controller or combination of controllers may be separately packaged as a module suitable for integration into a complete system 100.

The memory 144 may include any storage medium known in the art suitable for storing program instructions executable by the associated one or more processors 142. For example, the memory 144 may include a non-transitory memory medium. As an additional example, the memory 144 may include, but is not limited to, a read-only memory, a random access memory, a magnetic or optical memory device (e.g., disk), a magnetic tape, a solid state drive and the like. It is further noted that memory 144 may be housed in a common controller housing with the one or more processors 142. In one embodiment, the memory 144 may be located remotely with respect to the physical location of the one or more processors 142 and controller 130. For instance, the one or more processors 142 of controller 130 may access a remote memory (e.g., server), accessible through a network (e.g., internet, intranet and the like). Therefore, the above description should not be interpreted as a limitation on the present invention but merely an illustration.

Referring again to FIG. 2, in one embodiment, the dispersive element 132 is dynamically configurable. In this regard, the operation of the dispersive element 132 (e.g. the dispersion value, the exit angle of a particular wavelength of light, or the like) may be configurable and/or selectable. For example, a series of diffractive optical elements with different dispersion values (e.g. a series of diffraction gratings with different values of linear dispersion, or the like) may be mounted to a translatable assembly (not shown) such that the dispersion value of the hyperspectral imaging sub-system 106 may be dynamically modified. The translatable assembly may be any type of translatable assembly known in the art suitable for configuring the dispersive element 132 of the hyperspectral imaging sub-system 106. For example, the translatable assembly may include, but is not limited to, a rotational assembly or a linear translator. Further, the translatable assembly may include a manually translatable assembly, a motorized translatable assembly, or the like.

In another embodiment, the dispersion of a dynamically generated dispersive element 132 (e.g. an acousto-optic modulator, an electro-optic modulator, or the like) may be dynamically modified. For example, a modulation frequency of a transducer may be dynamically adjusted to modify the path of spectrally-dispersed sample radiation 122 from the dispersive element 132.

Figure 6:
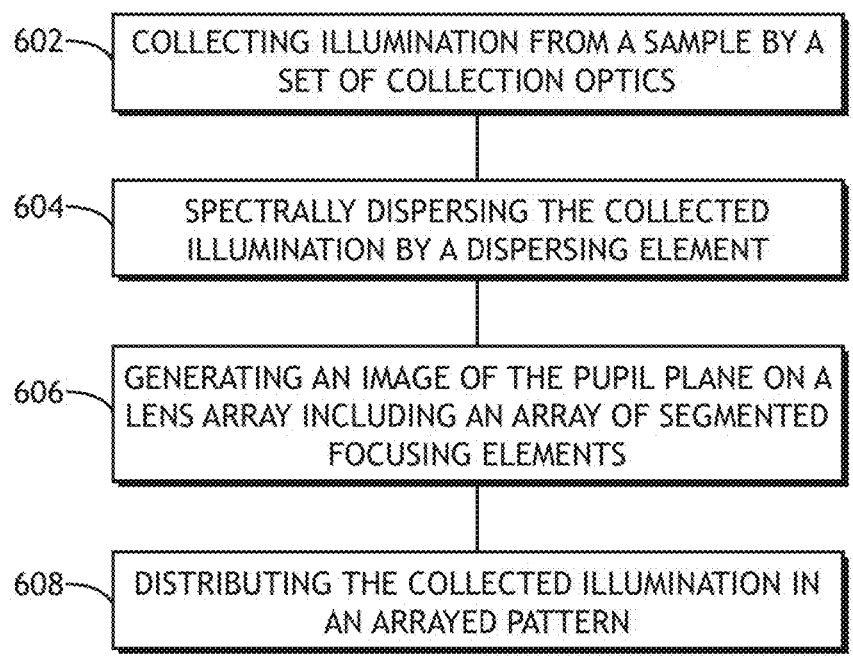
FIG. 6 is a flow diagram illustrating steps performed in a method, in accordance with one or more embodiments of the present disclosure.

FIG. 6 is a flow diagram illustrating steps performed in a method 600, in accordance with one or more embodiments of the present disclosure. Applicant notes that the embodiments and enabling technologies described previously herein in the context of system 100 should be interpreted to extend to method 600. It is further noted, however, that the method 600 is not limited to the architecture of system 100.

In one embodiment, the method 600 includes step 602 of collecting illumination from a sample by a set of collection optics. For example, one or more collection optics may collect illumination (e.g. sample radiation 122) from a sample at multitude of scattering angles (e.g. illumination from an illumination source scattered, reflected and/or diffracted by the sample). Further, the angular distribution of illumination collected by a sample may be represented as a spatial distribution of illumination (e.g. in a pupil plane, a back focal plane, a diffraction plane, or the like).

In another embodiment, the method 600 includes step 604 of spectrally dispersing the collected illumination by a dispersing element. For example, a dispersing element may be positioned at a pupil plane. Accordingly, the dispersing element may spectrally disperse the pupil plane according to the spectral content of the collected illumination.

In another embodiment, the method 600 includes step 606 of generating an image of the pupil plane on a lens array of focusing elements. For example, the spectrally-dispersed collected illumination may be combined to form the image of the pupil plane on the lens array.

In another embodiment, the method 600 includes step 608 of distributing the collected illumination in an arrayed pattern. For example, the lens array may divide the pupil plane (e.g. the image of the pupil plane on the lens array) into multiple segments according to the distribution of focusing elements. Accordingly, each focusing element of the lens array may collect and distribute a portion of the pupil plane such that the collected illumination forms an arrayed pattern (e.g. on a detector, another optical element, or the like). In another embodiment, the array pattern is spectrally dispersed. For example, each spectral portion (e.g. wavelength of sample radiation 122) may be associated with an array pattern and the array patterns corresponding to multiple spectral portions may be spatially displaced. In this regard, a detector may simultaneously capture illumination associated with the pupil plane for a multitude of wavelengths associated with the sample radiation 122. In another embodiment, each element of the array pattern (e.g. the array pattern for a given spectral portion) may include a scaled image of a portion of the pupil plane. Further, multiple images of illumination associated with the pupil plane (e.g. a pupil plane, or the like) may be simultaneously captured.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A metrology system, comprising:
an illumination source configured to generate an illumination beam;
one or more illumination optics configured to direct the illumination beam to a sample;
one or more collection optics configured to collect illumination emanating from the sample;
a detector; and
a hyperspectral imaging sub-system, comprising:
a dispersive element positioned at a pupil plane of the set of collection optics configured to spectrally disperse the collected illumination;
a lens array including an array of focusing elements; and
one or more imaging optics, wherein the one or more imaging optics combine the spectrally-dispersed collected illumination to form an image of the pupil plane on the lens array, wherein the focusing elements of the lens array segment the image of the pupil plane and distribute illumination from segments of the image of the pupil plane on the detector in an arrayed pattern based on a spatial distribution of the focusing elements of the lens array.

2. The metrology system of claim 1, wherein the arrayed pattern on the detector is spectrally dispersed.

3. The metrology system of claim 2, wherein a first portion of the arrayed pattern associated with a first wavelength of the collected illumination is spatially displaced with respect to a second portion of the arrayed pattern associated with a second wavelength of the collected illumination.

4. The metrology system of claim 3, wherein the first portion of the arrayed pattern and the second portion of the arrayed pattern are spatially distributed on the detector in a non-overlapping distribution.

5. The metrology system of claim 1, wherein the hyperspectral imaging sub-system further comprises:
a filter positioned at a plane conjugate to the sample, wherein the plane conjugate to the sample is associated with a spectrally-dispersed image of the sample, wherein the filter passes a selected portion of the collected illumination.

6. The metrology system of claim 5, wherein the filter includes a spatial filter to limit the spatial extent of the collected illumination.

7. The metrology system of claim 5, wherein the filter includes a spatial light modulator.

8. The metrology system of claim 1, wherein the lens array includes a one-dimensional lens array.

9. The metrology system of claim 8, wherein the lens array includes a cylindrical lens array.

10. The metrology system of claim 1, wherein the lens array includes a two-dimensional lens array.

11. The metrology system of claim 1, wherein the dispersive element comprises:
a diffraction grating.

12. The metrology system of claim 11, wherein the diffraction grating comprises:
at least one of a blazed diffraction grating, a ruled diffraction grating, or a holographic diffraction grating.

13. The metrology system of claim 1, wherein the dispersive element comprises:
an acousto-optic modulator.

14. The metrology system of claim 1, wherein the illumination source comprises:
a supercontinuum laser source.

15. A hyperspectral imaging apparatus, comprising:
a dispersive element configured to be positioned at a pupil plane of a set of collection optics, wherein the set of collection optics are configured to collect illumination emanating from a sample, wherein the dispersive element is configured to spectrally disperse the collected illumination;
a lens array including an array of focusing elements; and
one or more imaging optics, wherein the one or more imaging optics collect the spatially-dispersed set of wavelengths to generate an image of the pupil plane on the lens array, wherein the focusing elements of the lens array are configured to segment the image of the pupil plane and distribute illumination from segments of the image of the pupil plane in an arrayed pattern based on a distribution of the focusing elements of the lens array.

16. The hyperspectral imaging apparatus of claim 15, wherein the arrayed pattern is spectrally dispersed.

17. The hyperspectral imaging apparatus of claim 16, wherein a first portion of the arrayed pattern associated with a first wavelength of the collected illumination is spatially displaced with respect to a second portion of the arrayed pattern associated with a second wavelength of the collected illumination.

18. The hyperspectral imaging apparatus of claim 17, wherein the first portion of the arrayed pattern and the second portion of the arrayed pattern are spatially distributed in a non-overlapping distribution.

19. The hyperspectral imaging apparatus of claim 15, wherein the hyperspectral imaging sub-system further comprises:
a filter positioned at a plane conjugate to the sample, wherein the plane conjugate to the sample is associated with a spectrally-dispersed image of the sample, wherein the filter passes a selected portion of the collected illumination.

20. The hyperspectral imaging apparatus of claim 19, wherein the filter includes a spatial filter to limit the extent of the collected illumination.

21. The hyperspectral imaging apparatus of claim 19, wherein the filter includes a spatial light modulator.

22. The hyperspectral imaging apparatus of claim 15, wherein the lens array includes a one-dimensional lens array.

23. The hyperspectral imaging apparatus of claim 22, wherein the lens array includes a cylindrical lens array.

24. The hyperspectral imaging apparatus of claim 15, wherein the lens array includes a two-dimensional lens array.

25. The hyperspectral imaging apparatus of claim 15, wherein the dispersive element comprises:
a diffraction grating.

26. The hyperspectral imaging apparatus of claim 25, wherein the diffraction grating comprises:
at least one of a blazed diffraction grating, a ruled diffraction grating, or a holographic diffraction grating.

27. The hyperspectral imaging apparatus of claim 15, wherein the dispersive element comprises:
an acousto-optic modulator.

28. A metrology system, comprising:
an illumination source configured to generate an illumination beam;
one or more illumination optics configured to direct the illumination beam to a sample;
one or more collection optics configured to collect illumination emanating from the sample;
a hyperspectral imaging sub-system to generate a set of interleaved pupil images, wherein individual pupil images of the set of interleaved pupil images are representative of an angular distribution of the collected illumination from the one or more collection optics having a particular spectral range of wavelengths; and
a detector configured to capture the set of interleaved pupil images.

29. The metrology system of claim 28, wherein a first pupil image of the set of interleaved pupil images includes a first array of image segments, wherein a second pupil image of the set of interleaved pupil images includes at least a second array of image segments, wherein the first array of image segments is interleaved with at least the second array of image segments on the detector.

30. The metrology system of claim 28, wherein the particular spectral ranges of wavelengths of the individual pupil images are non-overlapping.

31. A method, comprising:
- collecting illumination from a sample by a set of collection optics;
- spectrally dispersing the collected illumination by a dispersing element, wherein the dispersing element is positioned at a pupil plane of the set of collection optics;
- generating an image of the pupil plane on a lens array including an array of focusing elements, wherein the spectrally-dispersed set collected illumination is combined to form the image of the pupil plane, wherein the focusing elements of the lens array segment the image of the pupil plane; and
- distributing illumination from segments of the image of the pupil plane in an arrayed pattern based on a distribution of the focusing elements of the lens array.

32. The method of claim 31, wherein distributing the collected illumination in an arrayed pattern comprises:
- distributing the collected illumination in a spectrally-dispersed arrayed pattern.

33. The metrology system of claim 1, wherein the image of the pupil plane on the lens array is spectrally de-dispersed.

* * * * *